(12) United States Patent
Scanlon et al.

(10) Patent No.: US 9,186,690 B2
(45) Date of Patent: Nov. 17, 2015

(54) ERGONOMIC HAND-OPERABLE FLUID-DISPENSING DEVICE

(75) Inventors: Christopher M. Scanlon, Milford, CT (US); Patrick J. McCormick, Honeoye Falls, NY (US); Dana Matsuzaki, Zollikon-ZH (CH)

(73) Assignee: Bausch & Lomb Incorporated, Rochester, NY (US)

( * ) Notice: Subject to any disclaimer, the term of this patent is extended or adjusted under 35 U.S.C. 154(b) by 622 days.

(21) Appl. No.: 13/018,889

(22) Filed: Feb. 1, 2011

(65) Prior Publication Data

US 2012/0197219 A1 Aug. 2, 2012

(51) Int. Cl.
*A61F 9/00* (2006.01)
*B05B 11/02* (2006.01)
*B05B 11/00* (2006.01)

(52) U.S. Cl.
CPC ............ *B05B 11/305* (2013.01); *A61F 9/0008* (2013.01); *B05B 11/0021* (2013.01); *B05B 11/0059* (2013.01); *B05B 11/304* (2013.01); *B05B 11/3052* (2013.01); *B05B 11/3094* (2013.01); *B05B 11/307* (2013.01)

(58) Field of Classification Search
CPC ..................... A61F 9/0008; B05B 11/3052
USPC ................... 604/294, 296–302; D24/120
See application file for complete search history.

(56) References Cited

U.S. PATENT DOCUMENTS

| | | | |
|---|---|---|---|
| 180,036 A * | 7/1876 | Jones | 222/320 |
| 185,180 A * | 12/1876 | Jones | 222/320 |
| 1,989,714 A * | 2/1935 | Statham | 222/490 |
| 3,170,462 A * | 2/1965 | Hall | 128/200.23 |
| 4,830,284 A * | 5/1989 | Maerte | 239/333 |
| 4,951,840 A | 8/1990 | Brison | |
| 4,973,322 A * | 11/1990 | Jewart | 604/300 |
| 5,024,355 A | 6/1991 | Jouillat et al. | |
| 5,267,986 A * | 12/1993 | Py | 604/294 |
| 5,373,972 A * | 12/1994 | Bystrom et al. | 222/212 |
| 5,588,564 A * | 12/1996 | Hutson et al. | 222/383.1 |
| 5,611,788 A * | 3/1997 | Marchment | 604/295 |
| 5,614,172 A * | 3/1997 | Geimer | 424/45 |
| 5,746,728 A * | 5/1998 | Py | 604/298 |
| 6,308,867 B1 * | 10/2001 | Wolter | 222/321.6 |
| 6,336,917 B1 * | 1/2002 | Berke | 604/295 |
| 6,386,397 B2 * | 5/2002 | Brotspies et al. | 222/321.6 |
| 6,419,124 B1 | 7/2002 | Hennemann et al. | |
| 6,851,583 B2 | 2/2005 | Masuzzo et al. | |
| 6,857,427 B2 * | 2/2005 | Ziegler et al. | 128/200.23 |
| 2002/0148462 A1 * | 10/2002 | Fugelsang et al. | 128/200.14 |
| 2004/0111070 A1 * | 6/2004 | Hanley | 604/295 |

(Continued)

FOREIGN PATENT DOCUMENTS

| | | |
|---|---|---|
| GB | 645149 A | 10/1950 |
| WO | WO 2010/139883 A1 | 12/2010 |

*Primary Examiner* — Tan-Uyen (Jackie) T Ho
*Assistant Examiner* — Paula L Craig
(74) *Attorney, Agent, or Firm* — Toan P. Vo

(57) ABSTRACT

A hand-operable system for ejecting a fluid composition into an eye, the system including: (1) a container having a container opening and containing the fluid composition; (2) a double-acting pump mechanism securely disposed over the container opening; and (3) an actuator that is disposed over, and extends radially outward from, the pump mechanism, for actuating the pump mechanism by applying a force thereon, wherein the pump mechanism includes a passage for the fluid composition, and the passage is positively sealed off when the application of the force is discontinued.

2 Claims, 4 Drawing Sheets

(56) References Cited

U.S. PATENT DOCUMENTS

| | | | |
|---|---|---|---|
| 2004/0173642 A1* | 9/2004 | Clifford et al. | 222/420 |
| 2005/0161467 A1* | 7/2005 | Jones | 222/23 |
| 2006/0016833 A1 | 1/2006 | Greiner-Perth | |

\* cited by examiner

TOP VIEW

SIDE VIEWS

US 9,186,690 B2

ERGONOMIC HAND-OPERABLE FLUID-DISPENSING DEVICE

BACKGROUND OF THE INVENTION

The present invention relates to an ergonomic hand-operable fluid-dispensing device. In particular, the present invention relates to an ergonomic hand-operable double-acting system for administering a fluid composition to an eye.

Ophthalmic disorders often require topical administration of fluid compositions to the affected eye. The patient often must administer the medication on herself or himself. Typically, eye drops are simply contained in a squeezable multi-use bottle from which the eye drops are dispensed through a simple bored-through nozzle. However, such a squeezable multi-use bottle presents the risk of contamination of the medication remaining in the bottle because the liquid that is not ejected completely from the nozzle after each use tends to flow back into the bottle when air is drawn in.

A device that can minimize or eliminate such risk of contamination employs a double-acting pump for ejecting the liquid from a bottle. One such device is disclosed in U.S. Pat. No. 6,851,583, which is incorporated herein by reference in its entirety. However, the use of this device in the upside-down position for self administration of an eye drop is quite awkward, especially for patients with less flexibility.

Therefore, there is a continued need to provide a more ergonomic hand-operable device for self administration of a fluid composition into an eye. Moreover, it is also very desirable to provide such a device to patients with less flexibility to encourage compliance with the required treatment.

SUMMARY

In general, the present invention provides a hand-operable device or system that is easily used by a patient for self administration of a fluid composition into an eye.

In one aspect, the present invention provides an ergonomic hand-operable device or system that is easily used by a patient for self administration of a fluid composition into an eye.

In another aspect, such a device or system comprises a double-acting pump mechanism for ejecting the fluid composition into an eye.

In still another aspect, the double-acting pump mechanism is actuated by applying a force on an actuator that is disposed over, and extends radially outward from, said pump mechanism.

In still another aspect, the present invention provides an ergonomic hand-operable system that is easily used by a patient for self administration of a fluid composition into an eye. The system comprises: (1) a container having a container opening and containing the fluid composition; (2) a double-acting pump mechanism securely disposed over the container opening; and (3) an actuator that is disposed over, and extends radially outward from, said pump mechanism, for actuating the pump mechanism by applying a force thereon, wherein said pump mechanism comprises a passage for said fluid composition, and said passage is positively sealed off when the application of said force is discontinued.

Other features and advantages of the present invention will become apparent from the following detailed description and claims.

DETAILED DESCRIPTION

In general, the present invention provides a hand-operable device or system that is easily used by a patient for self administration of a fluid composition into an eye.

In one aspect, the present invention provides an ergonomic hand-operable device or system that is easily used by a patient for self administration of a fluid composition into an eye.

In another aspect, such a device or system comprises a double-acting pump mechanism for ejecting the fluid composition into an eye.

In still another aspect, the double-acting pump mechanism is actuated by applying a force on an actuator that is disposed over, and extends radially outward from, said pump mechanism.

In still another aspect, the present invention provides an ergonomic hand-operable system that is easily used by a patient for self administration of a fluid composition into an eye. The system comprises: (1) a container having a container opening and containing the fluid composition; (2) a double-acting pump mechanism securely disposed over the container opening; and (3) an actuator that is disposed over, and extends radially outward from, said pump mechanism, for actuating the pump mechanism by applying a force thereon, wherein said pump mechanism comprises a passage for said fluid composition, and said passage is positively sealed off when the application of said force is discontinued.

In a further aspect, the present invention provides an ergonomic hand-operable system that is easily used by a patient for self administration of a fluid composition into an eye. The system comprises: (1) a container having a container opening and containing the fluid composition; (2) a double-acting pump mechanism securely disposed over the container opening; and (3) an actuator that is disposed over, and extends radially outward from, said pump mechanism, for actuating the pump mechanism by applying an actuating force thereon, wherein said pump mechanism comprises a passage for said fluid composition, and said passage is positively sealed off by longitudinal displacement of a piston over said passage under the restoring force of a spring when the application of said actuating force is discontinued.

An example of a double acting pump mechanism suitable for use with a device of the present invention is disclosed in U.S. Pat. No. 6,851,583, which is incorporated herein by reference in its entirety.

Figure 1:
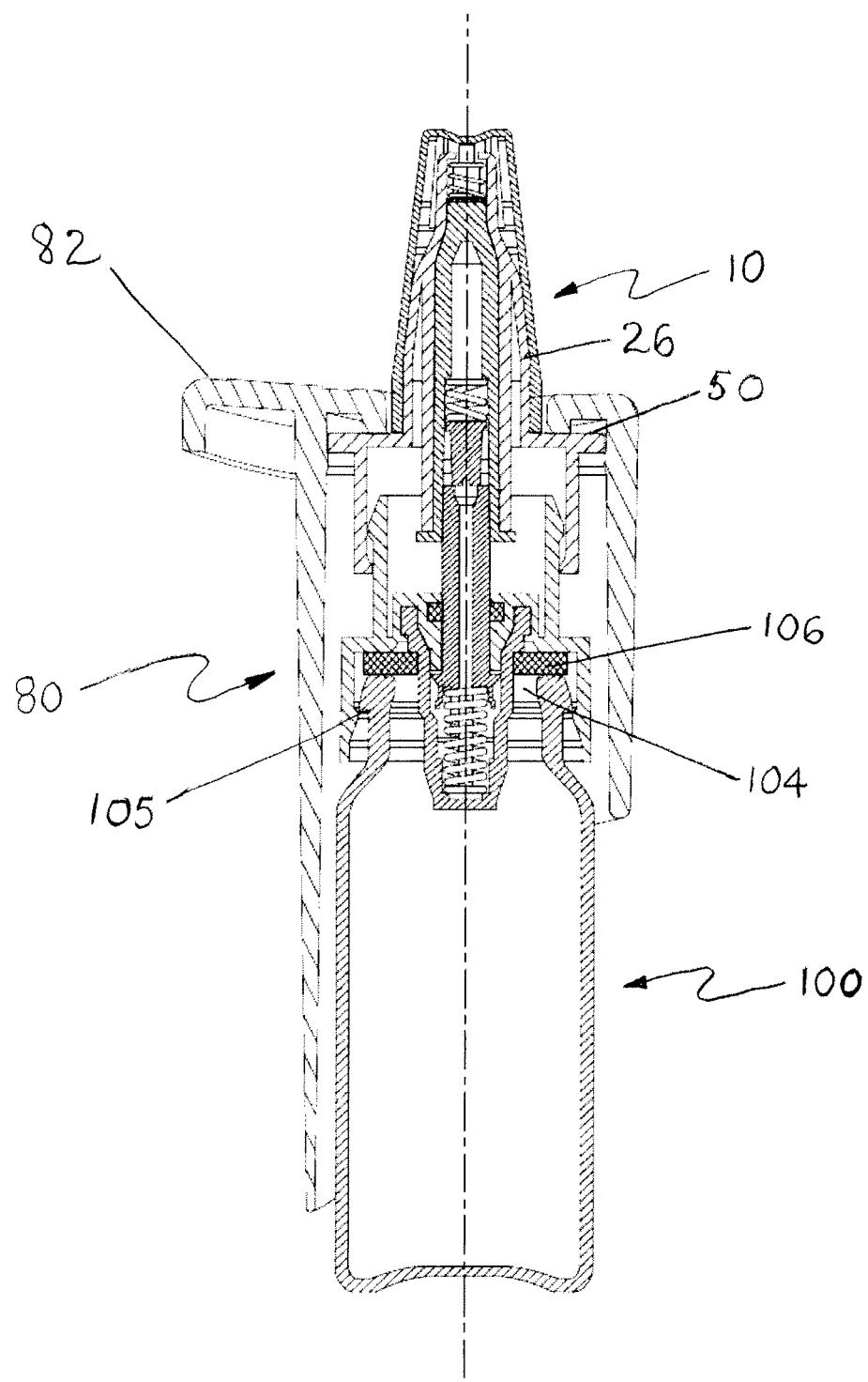
FIG. 1 shows the cross section of a device of the present invention.

Reference is made to FIG. 1, which shows a cross section of a hand-operable device or system of the present invention. The device or system comprises: (1) container 100 having container opening 104 and containing a fluid composition; (2) double-acting pump mechanism 10 securely disposed over container opening 104; and (3) actuator 80 that is disposed over, and extends radially outward from, said pump mechanism 10, for actuating the pump mechanism 10 by applying a force thereon.

Figure 2:
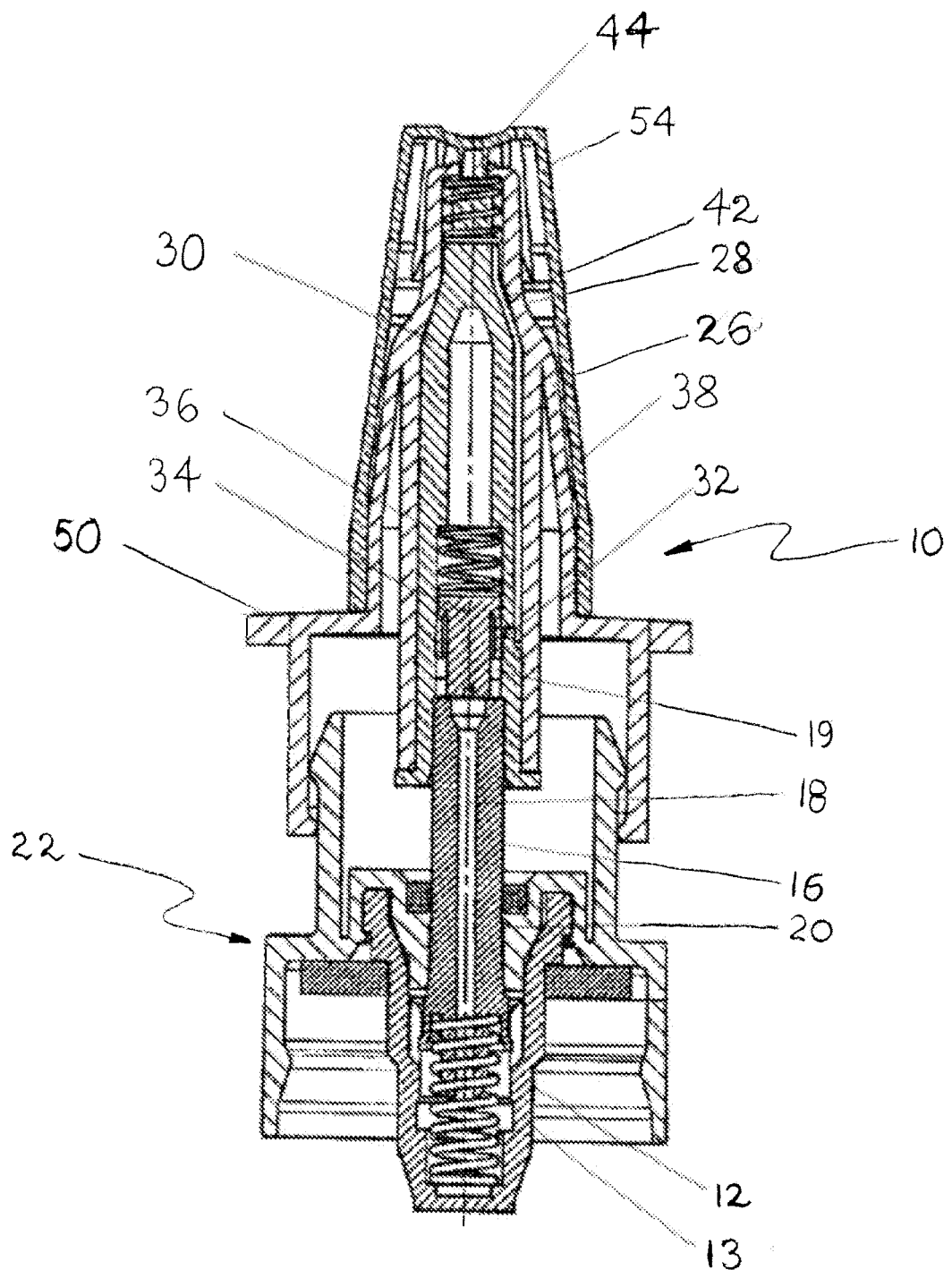
FIG. 2 shows detailed cross section of a double-acting pump mechanism that may be used in a device of the present invention.

Double-acting pump mechanism 10 is tightly attached by a snap seat on the slightly radially protruding rim 105 of opening 104 of container 100 through a sealing ring disk 106 disposed between pump mechanism 10 and container 100. Reference is made to FIG. 2, which shows a cross section of a double-acting pump mechanism that may be included in a device of the present invention. It should be understood that other designs of double-acting mechanisms may be equally suitable for inclusion in a device or system of the present invention. Double-acting pump mechanism 10 includes a cup-shaped housing 12. A hollow cylindrical piston 16 is axially displaceable in housing 12. Piston 16 is sealed relative to the inner side of housing 12 in a first housing portion 13. Bore 18 inside piston 16 extends axially and substantially through the length of piston 16. Bore 18 can communicate with the fluid in container 100 through, for example a transverse channel formed in the wall of first housing portion 13. Piston 16 is slidable in opening 20 of closing cap 22 that encloses housing 12 and securely and sealingly attaches double-acting mechanism 10 to container 100.

An actuating head 26 of double-acting pump mechanism 10 is tightly and securely placed on the free end of piston 16. Actuating head 26 comprises an outer sleeve 28 and an inner sleeve 30 tightly disposed concentrically inside outer sleeve 28. A small channel 19 is formed transversely through the wall of hollow piston 16 at the distal end thereof. A check valve 34 is fitted partially inside bore 18 at the distal end of hollow piston 16. When pump mechanism 10 is at rest, check valve 34 sealingly covers channel 19, preventing fluid from traversing therethrough. A restoring spring 36 is disposed on check valve 34 and rests against shoulder 38 formed inside inner sleeve 30.

A transverse bore 32 is formed through the wall of inner sleeve 30 at a small distance away from channel 19 such that check valve 34 covers both channel 19 and transverse bore 32 when pump mechanism 10 is at rest. Transverse bore 32 communicates with a longitudinal groove 42 formed on the outer surface of inner sleeve 30 to direct the fluid composition flowing through transverse bore 32 to fluid ejection opening 44 formed in the distal end of outer sleeve 28.

Actuating head 26 may be protected by a removable cap 54 when not in use.

When double-acting pump mechanism 10 is actuated, actuating head 26 is pushed toward bottle 100 against spring 36. As a result, channel 19 is aligned with transverse bore 32, allowing fluid to flow from bore 18 through hollow piston 16 and inner sleeve 30 to groove 42 toward ejection opening 44. When the force on spring 36 is removed, the restoring force of spring 36 moves actuating head 26 and piston 16 in opposite directions, and check valve 34 again covers both channel 19 and transverse bore 32, thereby cuts off the flow of fluid therethrough. In addition, an anti-microorganism material (such as silver) may be disposed in ejection opening 44 to prevent the growth of microorganisms therein between uses. Such anti-microorganism material may have an annular form, or is a disc made of a porous material having silver dispersed therein, fitted tightly in opening 44.

Reference is now made to FIG. 1, actuator 80 is disposed over pump mechanism 10, and extends radially outward therefrom, forming actuator shoulder 82. Pump mechanism 10 is actuated by, for example, applying a force on actuator shoulder 82. In the embodiment shown in FIG. 1, actuator 80 rests on shoulder 50 of actuating head 26. Actuator 80 extends longitudinally over at least a portion of bottle 100, for example, to provide stability during operation of pump 10.

Figure 3:
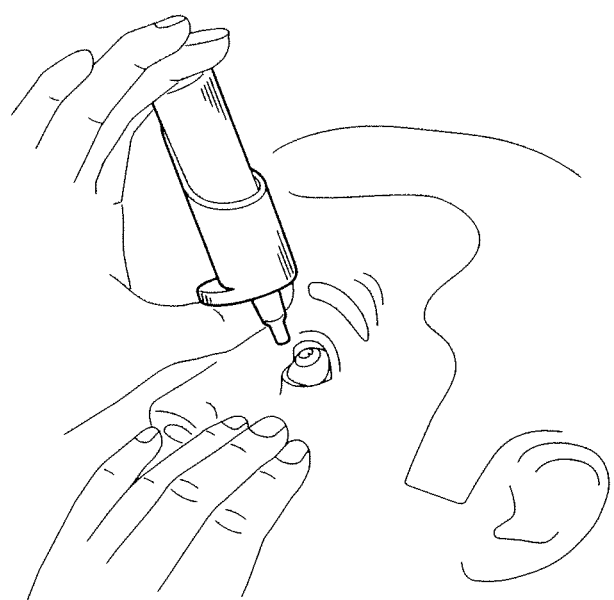
FIG. 3 shows operation of a device of the present invention during administration of an eye drop.
Figure 4:
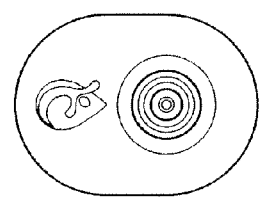
FIG. 4 shows various views of a device of the present invention, including the top view and several side views.
Figure 4:
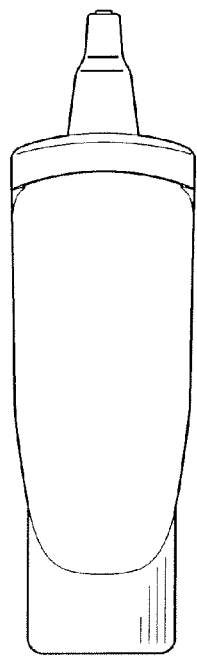
Figure 4:
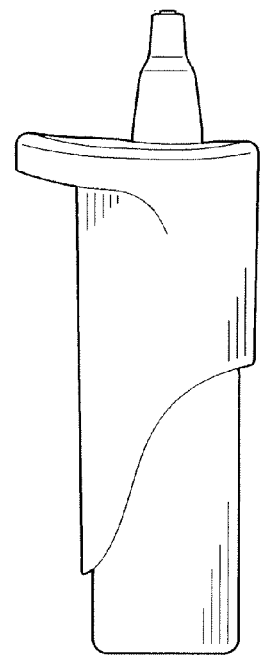
Figure 4:
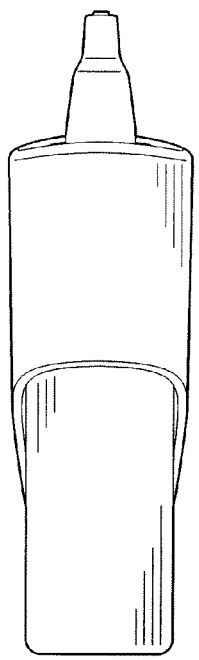

Reference is made to FIG. 3, wherein a typical operation of a device or system of the present invention is carried out for administration of an eye drop to a patient. For example, the patient holds the device in one hand with a thumb resting on the portion of the actuator that extends radially away from the bottle (actuator shoulder 82). The tip of the actuating head is directed to the eye. The pump mechanism is actuated by applying a force on the actuator to move the actuating head toward the bottle containing the eye drop composition. A drop of the fluid composition is ejected from the tip of actuating head 26 into the eye.

A system of the present invention is designed to be easily operated with one hand. For example, in one embodiment, the total length of the device in the unactuated state may be about 3.5-4.5 inches (or about 8.9-11.4 cm). The larger dimension of actuator shoulder 82 may be about 1.5-2 inches (or about 3.8-5 cm). The diameter of the bottle nay be about 1-1.5 inch (or about 2.5-3.8 cm), and the bottle may contain about 10-15 ml of the fluid composition.

One factor determining the amount of force required to operate pump 10 is the restoring force of spring 36. Actuator shoulder 82 is sized to accommodate a force applied by a thumb, and thus provides operational benefits especially to patients having limited flexibility.

The surface of actuator shoulder 82 on which a thumb rests may be provided with raised ridges or other similar designs to prevent slipping of the thumb. Alternatively, said surface may be formed with a friction enhancing material.

Bottle 100, actuator 80, and various parts of pump mechanism 10 may be made of polymeric materials, such as polyethylene (e.g., pharmaceutical-grade high-density polyethylene), polyvinyl chloride, or polyethylene terephthalate.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A hand-operable system for ejecting a fluid composition into an eye, the system comprising: (1) a container having a container opening and containing the fluid composition; (2) a double-acting pump mechanism securely disposed over the container opening; and (3) a single-piece actuator that is disposed over, and extends radially outward from, and to only one side of, said pump mechanism to form a shoulder that is sized to accommodate a thumb for actuating the pump mechanism by applying a force thereon; wherein said pump mechanism comprises a passage for said fluid composition, and said passage is positively sealed off when the application of said force is discontinued; wherein said actuator extends longitudinally from the shoulder over a substantial length portion of only one side of the container further than an opposite side of the container; and wherein said one side of the container is the same side as the shoulder.

2. The hand-operable system of claim 1, wherein the system is sized to be operated with one hand.

* * * * *